US011883635B2

United States Patent
Shluzas

(10) Patent No.: US 11,883,635 B2
(45) Date of Patent: Jan. 30, 2024

(54) SYSTEM AND METHOD FOR MICRODOSE INJECTION

(71) Applicant: CREDENCE MEDSYSTEMS, INC., Menlo Park, CA (US)

(72) Inventor: Alan E. Shluzas, San Carlos, CA (US)

(73) Assignee: Credence MedSystems, Menlo Park, CA (US)

( * ) Notice: Subject to any disclaimer, the term of this patent is extended or adjusted under 35 U.S.C. 154(b) by 206 days.

(21) Appl. No.: 17/351,006

(22) Filed: Jun. 17, 2021

(65) Prior Publication Data
US 2021/0393883 A1 Dec. 23, 2021

Related U.S. Application Data

(60) Provisional application No. 63/040,384, filed on Jun. 17, 2020.

(51) Int. Cl.
*A61M 5/315* (2006.01)
*A61M 5/31* (2006.01)

(52) U.S. Cl.
CPC .... *A61M 5/31531* (2013.01); *A61M 5/31501* (2013.01); *A61M 5/31505* (2013.01); *A61M 2005/3139* (2013.01)

(58) Field of Classification Search
CPC ...... A61M 5/31531; A61M 2005/3139; A61M 5/31525; A61M 5/3153; A61M 5/31501;
(Continued)

(56) References Cited

U.S. PATENT DOCUMENTS

| 827,693 A | 7/1906 | Korb |
| 2,648,334 A | 8/1953 | Brown et al. |

(Continued)

FOREIGN PATENT DOCUMENTS

| EP | 0074842 | 3/1983 |
| EP | 0904792 | 3/1999 |

(Continued)

OTHER PUBLICATIONS

PCT International Search Report for PCT/US2021/037946, Applicant Credence Medsystems Inc., dated Oct. 6, 2021.
(Continued)

*Primary Examiner* — Amber R Stiles
*Assistant Examiner* — Hong-Van N Trinh
(74) *Attorney, Agent, or Firm* — Vista IP Law Group LLP

(57) ABSTRACT

A system for injecting includes a syringe body, a syringe interior, a syringe flange, and a stopper member and an injectable fluid disposed in the syringe interior. The system also includes a plunger member coupled to the stopper member. The system further includes a finger flange removably coupled to the syringe flange, the finger flange defining a pair of side openings and a pair of bumps adjacent respective side openings. Moreover, the system also includes a swing spacer rotatably coupled to the finger flange, the swing spacer defining a pair of arms, a pair of pivot pins, two pairs of slots, and a pair of indentations. The swing spacer is configured to define a distance of movement of the plunger member relative to the syringe body along a longitudinal axis of the syringe body, thereby defining a dose of the injectable fluid.

15 Claims, 15 Drawing Sheets

(58) Field of Classification Search
CPC .... A61M 2005/31506; A61M 5/31535; A61M 5/31563; A61M 5/31571; A61M 5/31573; A61M 5/31591; A61M 5/3146; A61M 5/3159; A61M 5/31595
See application file for complete search history.

(56) References Cited

U.S. PATENT DOCUMENTS

| | | | |
|---|---|---|---|
| 2,771,217 | A | 11/1956 | Brown et al. |
| 2,933,087 | A | 4/1960 | Hamilton |
| 3,153,496 | A | 10/1964 | Johnson |
| 3,216,616 | A | 11/1965 | Blankenship, Jr. |
| 3,770,026 | A | 11/1973 | Isenberg |
| 3,815,785 | A | 6/1974 | Gilmont |
| 3,921,864 | A | 11/1975 | Dawes |
| 3,923,207 | A | 12/1975 | Kyogoku |
| 4,073,321 | A | 2/1978 | Moskowitz |
| 4,194,505 | A | 3/1980 | Schmitz |
| 4,370,982 | A | 2/1983 | Reilly |
| 4,384,581 | A | 5/1983 | Conway |
| 4,563,178 | A | 1/1986 | Santeramo |
| 4,973,318 | A | 11/1990 | Holm et al. |
| 5,271,527 | A | 12/1993 | Haber et al. |
| 5,304,152 | A | 4/1994 | Sams |
| 5,433,352 | A | 7/1995 | Ronvig |
| 5,667,495 | A | 9/1997 | Bitdinger et al. |
| 5,743,889 | A | 4/1998 | Sams |
| 5,833,669 | A | 11/1998 | Wyrick |
| 5,951,526 | A * | 9/1999 | Korisch ............ A61M 15/0026 604/232 |
| 5,961,495 | A | 10/1999 | Walters et al. |
| 6,126,644 | A | 10/2000 | Naganuma |
| 7,329,241 | B2 | 2/2008 | Horvath et al. |
| 7,678,084 | B2 | 3/2010 | Judson et al. |
| 8,361,036 | B2 | 1/2013 | Moller et al. |
| 8,529,521 | B2 | 9/2013 | Erickson et al. |
| 9,220,631 | B2 | 12/2015 | Sigg et al. |
| 9,345,842 | B2 | 5/2016 | Chanoch et al. |
| 9,566,387 | B2 | 2/2017 | Verhoeven et al. |
| 11,090,445 | B2 | 8/2021 | Diaz et al. |
| 2003/0032928 | A1 | 2/2003 | Sudo et al. |
| 2006/0129108 | A1 | 6/2006 | Vetter et al. |
| 2006/0200077 | A1 | 9/2006 | Righi et al. |
| 2006/0206057 | A1 | 9/2006 | Deruntz et al. |
| 2007/0265579 | A1 | 11/2007 | Kleyman et al. |
| 2008/0221530 | A1 | 9/2008 | Glejbol et al. |
| 2008/0262435 | A1 | 10/2008 | Erickson et al. |
| 2010/0175779 | A1 | 7/2010 | Ogawa et al. |
| 2011/0046559 | A1 | 2/2011 | Lum et al. |
| 2013/0226091 | A1 | 8/2013 | Nzike et al. |
| 2016/0220761 | A1 | 8/2016 | Shetty et al. |
| 2016/0228643 | A1 | 8/2016 | Oberdorfer et al. |
| 2016/0263329 | A1 | 9/2016 | Young et al. |
| 2016/0293329 | A1 | 9/2016 | Young et al. |
| 2017/0216524 | A1 | 8/2017 | Haider et al. |
| 2018/0126085 | A1 * | 5/2018 | Bowman ........... A61M 5/31515 |
| 2018/0250474 | A1 | 9/2018 | Wei |
| 2019/0015597 | A1 | 1/2019 | Holmqvist et al. |
| 2020/0306453 | A1 | 10/2020 | Langley et al. |
| 2020/0324054 | A1 | 10/2020 | Helmer et al. |
| 2021/0106763 | A1 * | 4/2021 | Meyer ............... A61M 5/31536 |

FOREIGN PATENT DOCUMENTS

| | | |
|---|---|---|
| EP | 1260241 | 11/2002 |
| EP | 2328639 B1 | 6/2011 |
| EP | 2397173 A2 | 12/2011 |
| JP | 2006-506166 | 2/2006 |
| JP | 2015-500095 | 1/2015 |
| WO | WO 96/26754 | 9/1996 |
| WO | WO 2012/149040 A2 | 11/2012 |
| WO | WO 2015/073991 A1 | 5/2015 |
| WO | WO 2017/062304 A1 | 4/2017 |
| WO | WO 2017/168287 | 10/2017 |
| WO | WO 2017/180480 | 10/2017 |
| WO | WO 2017/204787 | 11/2017 |
| WO | WO 2018146589 | 8/2018 |

OTHER PUBLICATIONS

Notice of Allowance for U.S. Appl. No. 16/011,453 dated Apr. 14, 2021.
Non-Final Office Action for U.S. Appl. No. 16/683,126 dated Jul. 27, 2021.
Amendment Response to NFOA for U.S. Appl. No. 16/683,126 dated Oct. 27, 2021.
Non-Final Office Action for U.S. Appl. No. 16/011,453 dated Oct. 1, 2020.
Amendment Response to NFOA for U.S. Appl. No. 16/011,453 dated Jan. 4, 2021.
PCT International Search Report for PCT/US2018/038098, Applicant: Credence Medsystems, Inc., Form PCT/ISA/210 and 220, dated Nov. 6, 2018 (9pages).
PCT Written Opinion of the International Search Authority for PCT/US2018/038098, Applicant: Credence Medsystems, Inc., Form PCT/ISA/237, dated Nov. 6, 2018 (10pages).
PCT International Search Report and Written Opinion for International Appln. No. PCT/US2019/061310 dated Jun. 22, 2020.
Notice of Allowance for U.S. Appln. No. 16/683,126 dated Apr. 13, 2022.
Foreign NOA for JP Patent Appln. No. 2019-569308 dated Apr. 18, 2022 (with English translation).
Foreign OA for JP Patent Appln. No. 2022-100018 dated Aug. 8, 2023 (with English translation).
Foreign OA for JP Patent Appln. No. 2021-525106 dated Feb. 7, 2023 (with English translation).
Non-Final Office Action for U.S. Appl. No. 17/403,095 dated Aug. 14, 2023.
Foreign Response to JP Patent Appln. No. 2022-100018 dated Oct. 3, 2023 (with English translation of amended claims).
Foreign OA for JP Patent Appln. No. 2021-525106 dated Sep. 26, 2023 (with English translation).
Amendment Response to NFOA for U.S. Appl. No. 17/403,095 dated Nov. 14, 2023.

* cited by examiner

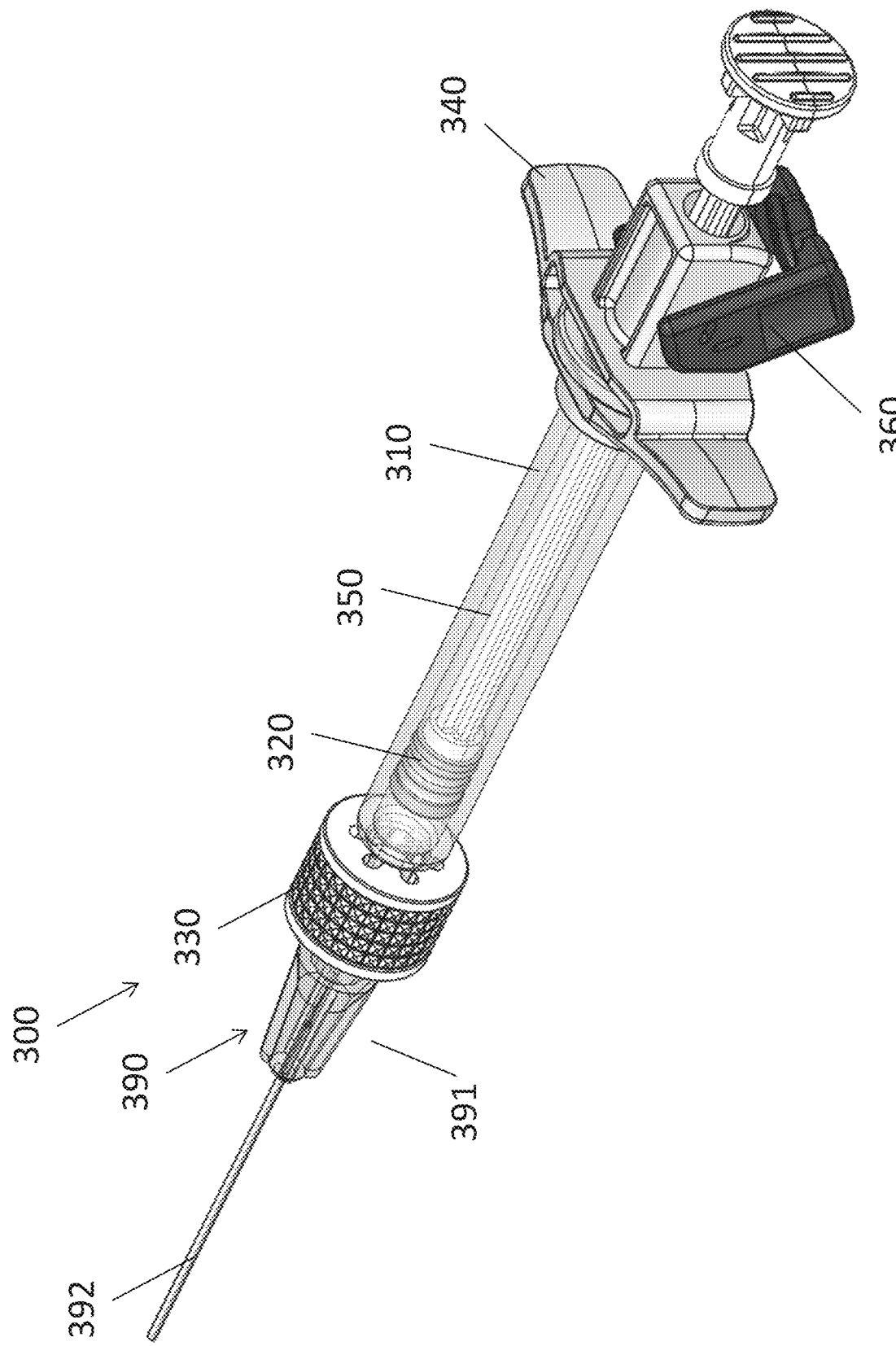

SYSTEM AND METHOD FOR MICRODOSE INJECTION

The present application claims priority to U.S. Provisional Patent Application Ser. No. 63/040,384, filed on Jun. 17, 2020 entitled "SYSTEM AND METHOD FOR MICRODOSE INJECTION." This application includes subject matter similar to the subject matter described in the following co-owned U.S. patent applications: (1) U.S. Utility patent application Ser. No. 16/683,126, filed on Nov. 13, 2019, and entitled "SYSTEM AND METHOD FOR MICRODOSE INJECTION"; (2) Ser. No. 14/696,342, filed Apr. 24, 2015, and entitled "SYSTEM AND METHOD FOR SAFETY SYRINGE"; (3) Ser. No. 14/543,787, filed Nov. 17, 2014, and entitled "SYSTEM AND METHOD FOR DRUG DELIVERY WITH A SAFETY SYRINGE"; (4) Ser. No. 14/321,706, filed Jul. 1, 2014, and entitled "SAFETY SYRINGE"; and (5) Ser. No. 62/416,102, filed Nov. 1, 2016, and entitled "SYSTEM AND METHOD FOR SAFETY SYRINGE"; (6) Ser. No. 62/431,382, filed Dec. 7, 2016, and entitled "SYSTEM AND METHOD FOR SAFETY SYRINGE"; (7) Ser. No. 62/480,276, filed Mar. 31, 2017, and entitled "SYSTEM AND METHOD FOR SAFETY SYRINGE; (8) Ser. No. 62/508,508, filed May 19, 2017, and entitled "SYSTEM AND METHOD FOR COLLECTING INJECTION INFORMATION"; (9) Ser. No. 62/542,230, filed Aug. 7, 2017, and entitled "CARTRIDGE SAFETY INJECTION SYSTEM AND METHODS"; (10) Ser. No. 15/801,239, filed Nov. 1, 2017, and entitled "SYSTEM AND METHOD FOR SAFETY SYRINGE"; (11) Ser. No. 15/801,259, filed Nov. 1, 2017, and entitled "SYSTEM AND METHOD FOR SAFETY SYRINGE"; (12) Ser. No. 15/801,281, filed Nov. 1, 2017, and entitled "CARTRIDGE SAFETY INJECTION SYSTEM AND METHODS"; (13) Ser. No. 15/801,304, filed Nov. 1, 2017, and entitled "SYSTEM AND METHOD FOR SAFETY SYRINGE"; (14) Ser. No. 16/011,453, filed Jun. 18, 2018, and entitled "SYSTEM AND METHOD FOR SAFETY SYRINGE"; (15) Ser. No. 15/985,354, filed May 21, 2018, and entitled "SYSTEM AND METHOD FOR COLLECTING INJECTION INFORMATION"; and "(16) Ser. No. 16/683,157, filed Nov. 13, 2019, and entitled "SYSTEM AND METHOD FOR MULTIPLE SITE INJECTION." The contents of the applications identified herein are fully incorporated herein by reference as though set forth in full.

FIELD OF THE INVENTION

The present invention relates generally to injection systems, devices, and processes for facilitating various levels of control over fluid infusion, and more particularly to systems and methods related to syringes for delivery microliter range doses of fluids in healthcare environments.

BACKGROUND

Millions of syringes, such as that depicted in FIG. 1A 2, are consumed in healthcare environments every day. A typical syringe 2 includes a tubular body 4, a plunger 6, and an injection needle 8. As shown in FIG. 1B, such a syringe 2 may be utilized not only to inject fluid into a patient, but also to withdraw or expel fluid out of or into a container such as a medicine bottle, vial, bag, or other drug containment system 10. Indeed, due to regulatory constraints in some countries such as the United States as well as sterility maintenance concerns, upon use of a medicine bottle 10 with a syringe 2 as shown in a particular patient's environment, such medicine bottle may only be utilized with a single patient and then must be disposed of—causing significant medical waste from bottle and remaining medicine disposal, and even contributing to periodic shortages of certain critical drugs.

Referring to FIG. 2A, three Luer-type syringes 12 are depicted, each having a Luer fitting geometry 14 disposed distally, so that they may be coupled with other devices having similar mating geometry, such as the Luer manifold assembly 16 depicted in FIG. 2B. The Luer manifold assembly of FIG. 2B may be used to administer liquid drugs to the patient intravenously with or without the use of an intravenous infusion bag. The Luer fittings 14 of the syringes of FIG. 2A may be termed the "male" Luer fittings, while those of FIG. 2B 18 may be termed the "female" Luer fittings; one of the Luer interfaces may be threaded (in which case the configuration may be referred to as a "Luer lock" configuration) so that the two sides may be coupled by relative rotation, which may be combined with compressive loading. In other words, in one Luer lock embodiment, rotation, possibly along with compression, may be utilized to engage threads within the male fitting 14 which are configured to engage a flange on the female fitting 18 and bring the devices together into a fluid-sealed coupling. In another embodiment, tapered interfacing geometries may be utilized to provide for a Luer engagement using compression without threads or rotation (such a configuration may be referred to as a "slip-on" or "conical" Luer configuration). While such Luer couplings are perceived to be relatively safe for operators, there is risk of medicine spilling/leaking and parts breakage during the loading to provide a Luer coupling. The use of needle injection configurations, on the other hand, carries with it the risk of a sharp needle contacting or poking a person or structure that is not desired. For this reason, so called "safety syringes" have been developed.

One embodiment of a safety syringe 20 is shown in FIG. 3, wherein a tubular shield member 22 is spring biased to cover the needle 8 when released from a locked position relative to the syringe body 4. Another embodiment of a safety syringe 24 is shown in FIGS. 4A-4B. With such a configuration, after full insertion of the plunger 6 relative to the syringe body 4, the retractable needle 26 is configured to retract 28, 26 back to a safe position within the tubular body 4, as shown in FIG. 4B. Such a configuration which is configured to collapse upon itself may be associated with blood spatter/aerosolization problems, the safe storage of pre-loaded energy which may possible malfunction and activate before desirable, loss of accuracy in giving full-dose injections due to residual dead space within the spring compression volume, and/or loss of retraction velocity control which may be associated with pain and patient anxiety.

Further complicating the syringe marketplace is an increasing demand for pre-filled syringe assemblies such as those depicted in FIGS. 5A and 5B, which generally include a syringe body, or "drug enclosure containment delivery system", 34, a plunger tip, plug, or stopper 36, and a distal seal or cap 35 which may be fitted over a Luer type interface (FIG. 5A shows the cap 35 in place; FIG. 5B has the cap removed to illustrate the Luer interface 14. Liquid medicine may reside in the volume, or medicine reservoir, 40 between the distal seal 35 and the distal end 37 of the stopper member 36. The stopper member 36 may include a standard butyl rubber material and may be coated, such as with a biocompatible lubricious coating (e.g., polytetrafluoroethylene ("PTFE")), to facilitate preferred sealing and relative motion characteristics against the associated syringe body 34 structure and material. The proximal end of the syringe body 34 in FIG. 5B includes a conventional integral syringe flange 38), which is formed integral to the material of the syringe body 34. The flange 38 is configured to extend radially from the syringe body 34 and may be configured to be a full circumference, or a partial circumference around the syringe body 34. A partial flange is known as a "clipped flange" while the other is known as a "full flange." The flange is used to grasp the syringe with the fingers to provide support for pushing on the plunger to give the injection. The syringe body 34 preferably includes a translucent material such as a glass or polymer. To form a contained volume within the medicine chamber or reservoir 40, and to assist with expulsion of the associated fluid through the needle, a stopper member 36 may be positioned within the syringe body 34. The syringe body may define a substantially cylindrical shape (i.e., so that a plunger tip 36 having a circular cross sectional shape may establish a seal against the syringe body), or be configured to have other cross sectional shapes, such as an ellipse.

Such assemblies are desirable because they may be standardized and produced with precision in volume by the few manufacturers in the world who can afford to meet all of the continually changing regulations of the world for filling, packaging, and medicine/drug interfacing materials selection and component use. Such simple configurations, however, generally will not meet the new world standards for single-use, safety, auto-disabling, and anti-needle-stick. Thus certain suppliers have moved to more "vertical" solutions, such as that 41 featured in FIG. 5C, which attempts to meet all of the standards, or at least a portion thereof, with one solution; as a result of trying to meet these standards for many different scenarios, such products may have significant limitations (including some of those described above in reference to FIGS. 3-4B) and relatively high inventory and utilization expenses.

Moreover, injection systems have reduced accuracy and precision as the volume of injectable fluid is reduced into the microliter range ("microdose"). In particular, removing air from the syringe body ("de-bubbling") before injection is difficult to perform accurately and precisely for such microdose injection systems.

There is a need for injection systems which address shortcomings of currently-available configurations. In particular, there is a need for injection systems that perform (de-bubble and inject) accurately in the microliter range. It is also desirable that such syringe assemblies may utilize the existing and relatively well-controlled supply chain of conventionally delivered pre-filled cartridges and other off-the-shelf components, and the corresponding assembly machinery and personnel.

SUMMARY

Embodiments are directed to injection systems. In particular, the embodiments are directed to microliter range injection systems that include at least some off-the-shelf syringe components.

In one embodiment, a system for injecting includes a syringe body having proximal and distal ends, a syringe interior, and a syringe flange at the proximal end thereof. The system also includes an injectable fluid disposed in the syringe interior. The system further includes a stopper member disposed in the syringe interior. Moreover, the system includes a plunger member coupled to the stopper member. In addition, the system includes a finger flange removably coupled to the syringe flange, the finger flange defining a pair of side openings and a pair of bumps adjacent respective side openings. The system also includes a swing spacer rotatably coupled to the finger flange, the swing spacer defining a pair of arms, a pair of pivot pins, two pairs of slots, and a pair of indentations. The swing spacer is configured to define a distance of movement of the plunger member relative to the syringe body along a longitudinal axis of the syringe body, thereby defining a dose of the injectable fluid.

In one or more embodiments, the pair of pivot pins on the swing spacer are disposed in the pair of side openings on the finger flange, such that the pair of side openings and the pair of pivot pins define a hinge about which the swing spacer rotates relative to the finger flange. Respective clearances between the pair of pivot pins and respective ones of the pair of side openings allow for axial movement of the swing spacer during priming of the system. The syringe body may also include a distal needle interface configured to be coupled to a needle assembly having a needle.

In one or more embodiments, the swing spacer has an aligned configuration wherein a longitudinal axis of the swing spacer is aligned with the longitudinal axis of the syringe body, and an askew configuration the longitudinal axis of the swing spacer is askew from the longitudinal axis of the syringe body. The swing spacer in the aligned configuration may limit distal movement of the plunger member relative to the syringe body. The swing spacer in the askew configuration may not limit distal movement of the plunger member relative to the syringe body, such that the swing spacer is configured to define a distance of movement of the plunger member relative to the syringe body along a longitudinal axis of the syringe body, thereby defining a dose of the injectable fluid.

In one or more embodiments, the two pairs of slots on the swing spacer include two aligned slots and two askew slots. The aligned slots are configured to interfere with the pair of bumps on the finger flange to removably retain the swing spacer in the aligned configuration. The askew slots are configured to interfere with the pair of bumps on the finger flange to removably retain the swing spacer in the askew configuration. The pair of indentations on the swing spacer may be configured to facilitate user manipulation of the swing spacer to move the swing spacer between the aligned and askew configurations In one or more embodiments, the swing spacer also includes a proximal surface when the swing spacer is in the aligned configuration. The plunger member may include a stop configured to interfere with the proximal surface on the swing spacer in the aligned configuration to limit distal movement of the plunger member relative to the syringe body.

In one or more embodiments, wherein the system has a transport configuration in which the swing spacer is in the aligned configuration and the stop on the plunger member is disposed a distance proximal of the proximal surface of the swing spacer. The system also has a primed configuration in which the swing spacer is in the aligned configuration and the stop on the plunger member is in contact with the proximal surface of the swing spacer. The system further has an injection configuration in which the swing spacer is in the askew configuration and the stop on the plunger member is disposed a distance proximal of with a proximal surface of the finger flange. Moreover, the system has a completed configuration in which the swing spacer is in the askew configuration and the stop on the plunger member is in contact with the proximal surface of the finger flange.

In another embodiment, a method for injecting a fluid includes providing a syringe assembly. The syringe assembly includes a syringe body having proximal and distal ends, a syringe interior, a distal needle interface at the distal end thereof, and a syringe flange at the proximal end thereof. The syringe assembly also includes an injectable fluid disposed in the syringe interior. The syringe assembly further includes a stopper member disposed in the syringe interior. Moreover, the syringe assembly includes a plunger member coupled to the stopper member. In addition, the syringe assembly includes a finger flange removably coupled to the syringe flange, the finger flange defining a pair of side openings and a pair of bumps adjacent respective side openings. The syringe assembly also includes a swing spacer rotatably coupled to the finger flange, the swing spacer defining a pair of arms, a pair of pivot pins, two pairs of slots, and a pair of indentations, the swing spacer being in an aligned configuration wherein a longitudinal axis of the swing spacer is aligned with a longitudinal axis of the syringe body. The method also includes moving the swing spacer from the aligned configuration to an askew configuration the longitudinal axis of the swing spacer is askew from the longitudinal axis of the syringe body. The method further includes applying a distally directed force to a proximal end of the plunger member to expel a portion of the injectable fluid from the syringe interior through the distal needle interface.

In one or more embodiments, wherein the system has a transport configuration in which the swing spacer is in the aligned configuration and the stop on the plunger member is disposed a distance proximal of a proximal surface of the swing spacer. The system also has a primed configuration in which the swing spacer is in the aligned configuration and the stop on the plunger member is in contact with the proximal surface of the swing spacer. The system further has an injection configuration in which the swing spacer is in the askew configuration and the stop on the plunger member is disposed a distance proximal of with a proximal surface of the finger flange. Moreover, the system has a completed configuration in which the swing spacer is in the askew configuration and the stop on the plunger member is in contact with the proximal surface of the finger flange.

In one or more embodiments, the syringe assembly is provided in the transport configuration. The method also includes positioning the syringe assembly in the transport configuration in an upright orientation before moving the swing spacer from the aligned configuration to the askew configuration. The method further includes applying a distally directed force to the proximal end of the plunger member to expel a gas from the syringe interior through the distal needle interface to transform the syringe assembly from the transport configuration to the primed configuration before moving the swing spacer from the aligned configuration to the askew configuration. Moving the swing spacer from the aligned configuration to the askew configuration transforms the syringe assembly from the primed configuration to the injection configuration. Applying the distally directed force to the proximal end of the plunger member to expel the portion of the injectable fluid from the syringe interior through the distal needle interface transforms the syringe assembly from the injection configuration to the completed configuration.

In one or more embodiments, the swing spacer in the aligned configuration limits distal movement of the plunger member relative to the syringe body. The swing spacer in the askew configuration does not limit distal movement of the plunger member relative to the syringe body, such that the swing spacer is configured to define a distance of movement of the plunger member relative to the syringe body along the longitudinal axis of the syringe body, thereby defining a dose of the injectable fluid.

In one or more embodiments, the two pairs of slots on the swing spacer include two aligned slots and two askew slots. The aligned slots are configured to interfere with the pair of bumps on the finger flange to removably retain the swing spacer in the aligned configuration. The askew slots are configured to interfere with the pair of bumps on the finger flange to removably retain the swing spacer in the askew configuration. Moving the swing spacer from the aligned configuration to the askew configuration may include grasping the pair of indentations on the swing spacer.

The aforementioned and other embodiments of the invention are described in the Detailed Description which follows.

BRIEF DESCRIPTION OF THE DRAWINGS

The foregoing and other aspects of embodiments are described in further detail with reference to the accompanying drawings, in which the same elements in different figures are referred to by common reference numerals, wherein:

FIGS. 6 and 7 are perspective and exploded views of a microdose injection system according to some embodiments.

Figure 1A:
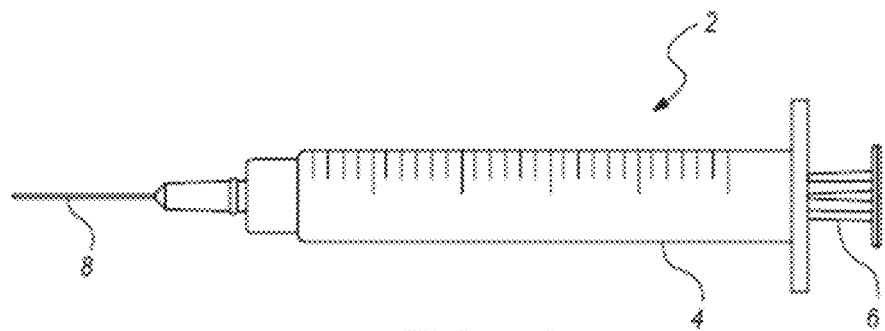
FIGS. 1A-5C illustrate various aspects of conventional injection syringe configurations.
Figure 1B:
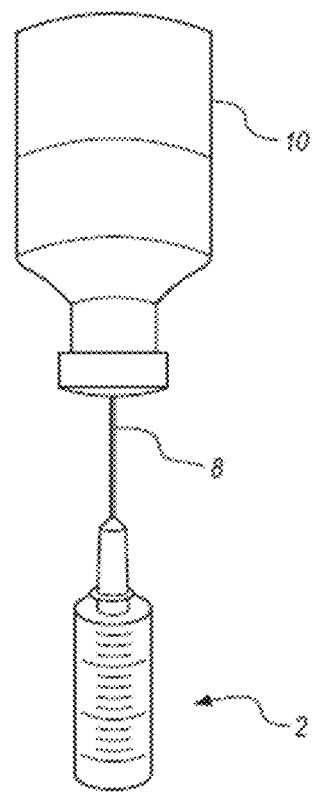
Figure 2A:
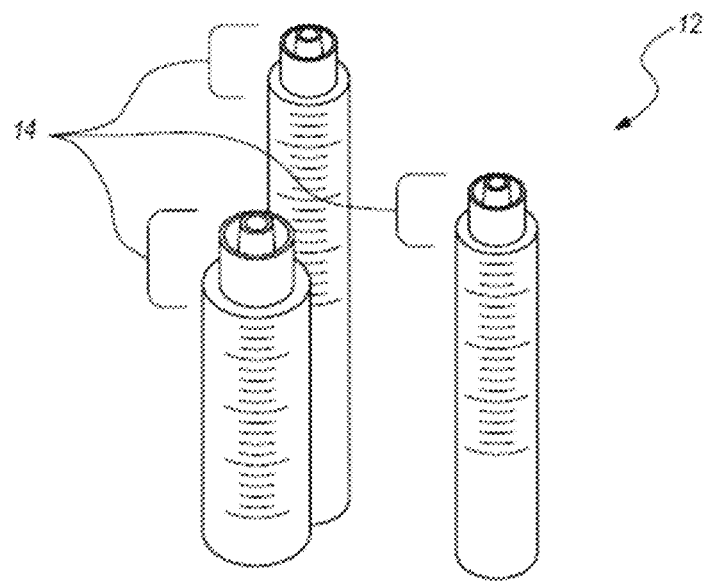
Figure 2B:
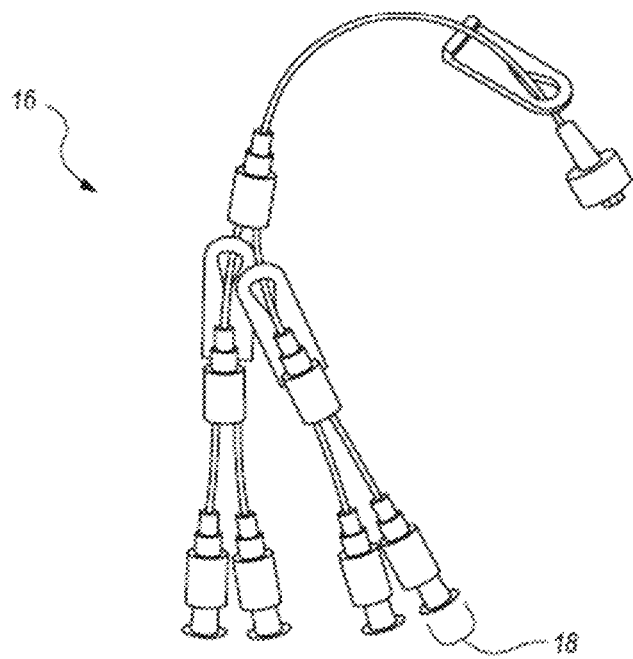
Figure 3:
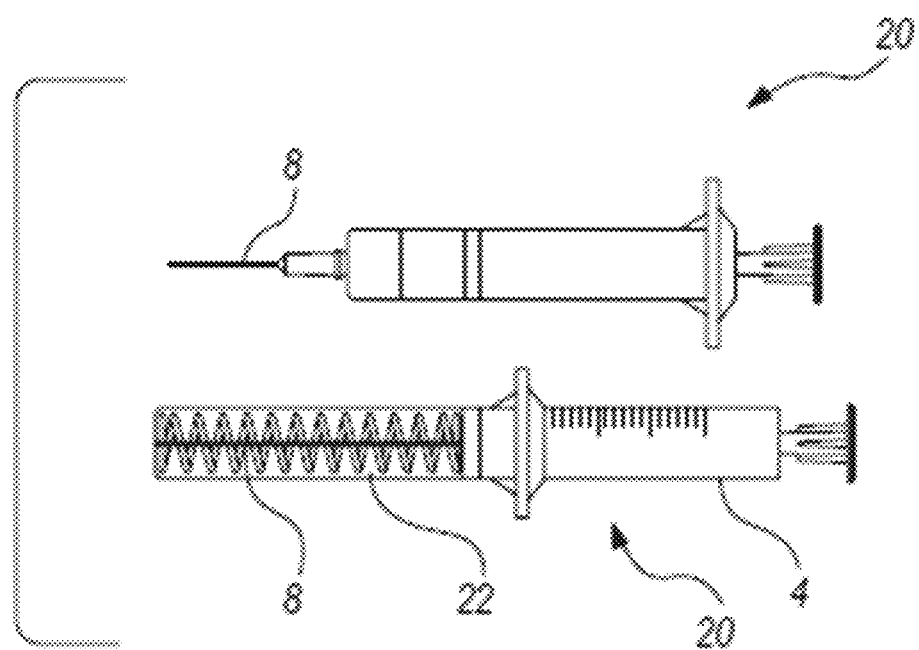
Figure 4A:
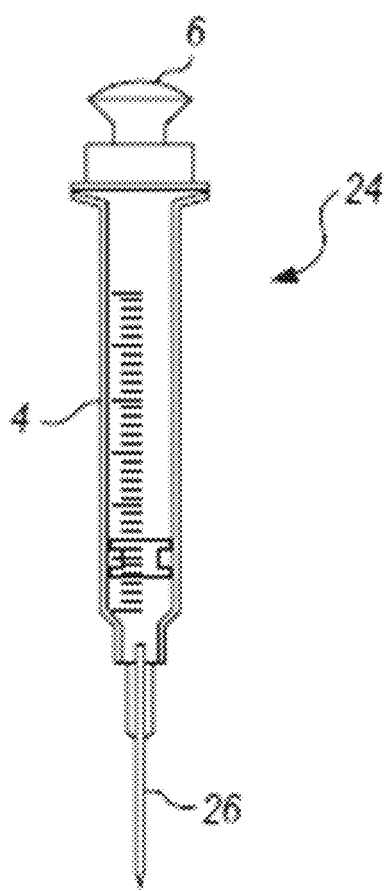
Figure 4B:
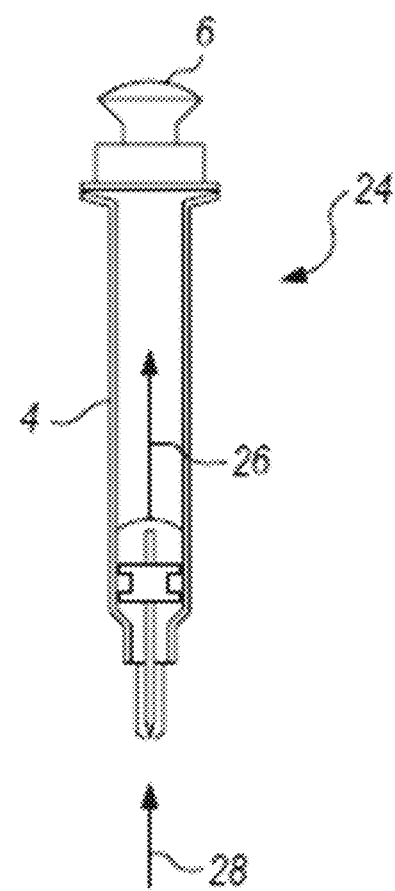
Figure 5A:
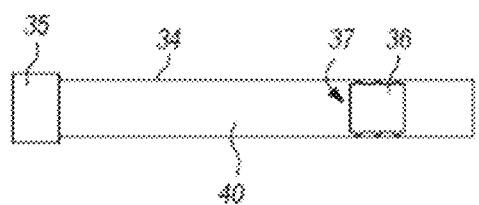
Figure 5B:
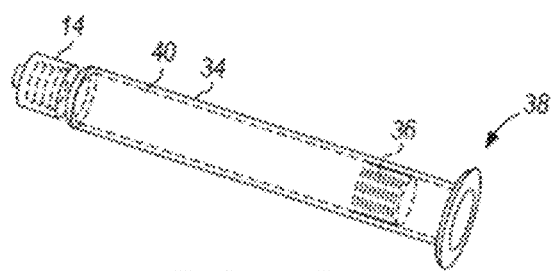
Figure 5C:
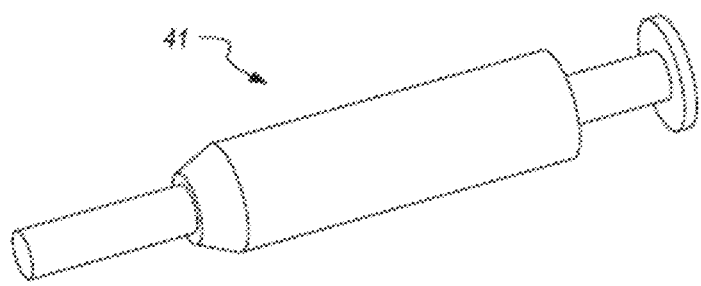

In order to better appreciate how to obtain the above-recited and other advantages and objects of various embodiments, a more detailed description of embodiments is provided with reference to the accompanying drawings. It should be noted that the drawings are not drawn to scale and that elements of similar structures or functions are represented by like reference numerals throughout. It will be understood that these drawings depict only certain illustrated embodiments and are not therefore to be considered limiting of scope of embodiments.

DETAILED DESCRIPTION OF ILLUSTRATED EMBODIMENTS

Exemplary Microdose Injection Systems

FIGS. 6-13 depict a microdose injection system 300 according to another embodiment. As used herein, the term "microdose" or "micro-dose" includes, but is not limited to, injections in the 1-1,000 microliter range. The microdose injection system 300 addresses the problem of injections in the microliter (e.g., 10 µL) volume range, which are difficult to accomplish with a standard injection system while maintaining precision (e.g., repeatability) and accuracy (e.g., proximity to desired volume). The microdose injection system 300 utilizes a rotatable swing spacer 360 and a fixed plunger member travel distance/gap to perform microdose injections.

Figure 7:
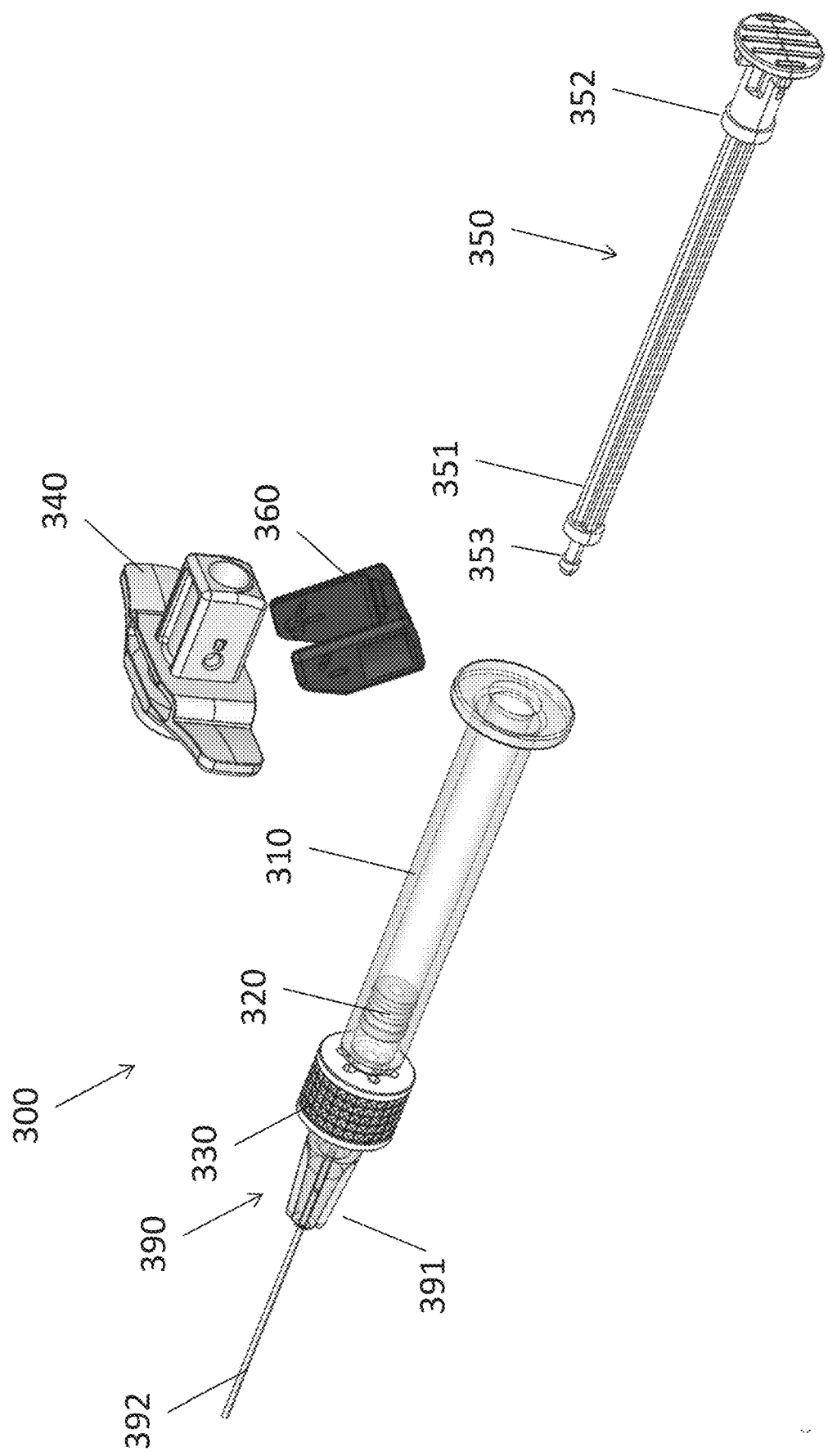

Like many of the injection systems described in co-owned U.S. patent application Ser. Nos. 14/696,342, 14/543,787, 14/321,706, 62/416,102, 62/431,382, 62/480,276, 62/508,508, 62/542,230, 15/801,239, 15/801,259, 15/801,281, 15/801,304, 16/011,453, 16/683,126, and 16/683,157, the contents of which were previously fully incorporated herein by reference as though set forth in full, the microdose injection system 300 utilizes off-the-shelf syringe bodies 310, stopper members 320, and distal needle interfaces 330. The microdose injection system 300 may also be used with off-the-shelf needle assemblies 390 including needle hubs 391 and needles 392. The finger flange 340 in the microdose injection system 300 includes a pair of side openings 342 configured to mate with a pair of pivot pins 362 on a swing spacer 360, as shown in FIGS. 7, 8, and 9.

The microdose injection system 300 includes a syringe body 310, a stopper member 320, a distal needle interface 330, a finger flange 340, a plunger member 350, a needle assembly 390, and a swing spacer 360. Many of these system components (e.g., the syringe body 310, the stopper member 320, and the distal needle interface 330) may be off-the-shelf components to utilize the existing and relatively well-controlled supply chain, and the corresponding assembly machinery and personnel. The stopper member 320 may have a hollow interior with an internal surface, which may have internal threads or may be un-threaded. The plunger member 350 is configured to have a distal end 351, and a stop 352. The plunger member 350 may be configured to include a stopper interface projection 353, for interface with the stopper member 320. Alternatively, the distal end of the plunger member may be smooth. The syringe body 310 may be an off-the-shelf 0.50 cc syringe body 310 to improve the accuracy of the microdose injection system 300. The needle assembly 390 may be a commercially available, off-the-shelf needle assembly with a needle 392 (e.g., 20-34 gauge and length 6 mm-⅝"; in particular 32 gauge x 6 mm length). The needle assembly 390 may utilize Luer lock or Luer slip configurations to attach the needle assembly 390 to the syringe body 310/distal needle interface 330. In some embodiments, microdose injection systems 300 can achieve error rates of less than ±10 µL.

Figure 8:
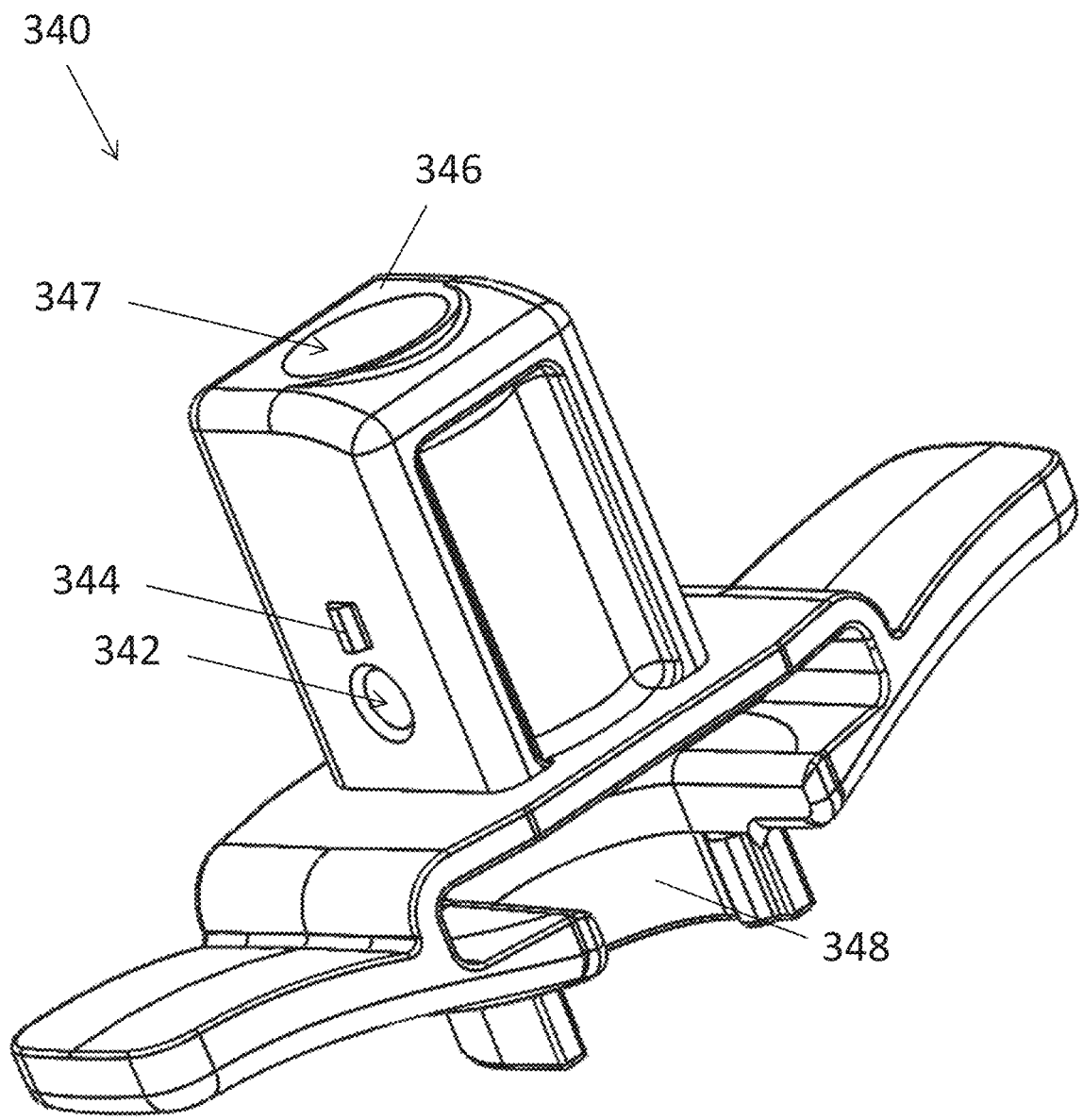
FIG. 8 is a perspective view of a finger flange for use with microdose injection systems according to some embodiments.

As shown in FIG. 8, the finger flange 340 includes a pair of side openings 342 and a pair of bumps 344 disposed adjacent to and proximal of corresponding ones of the pair side openings 342. The finger flange 340 also includes a proximal surface 346 configured to limit distal movement of the larger member 350 relative to the finger flange 340 and the syringe body 310 to which the finger flange 340 is coupled. The finger flange further includes an internal passage 347 configured to allow the plunger member distal end 351 to be inserted therethrough. The internal passage 347 is sized to be smaller than the stop 352 to prevent passage of the stop 352 through the internal passage 347. The finger flange also includes a syringe interface 348 for coupling to the proximal end of the syringe body 310.

Figure 9:
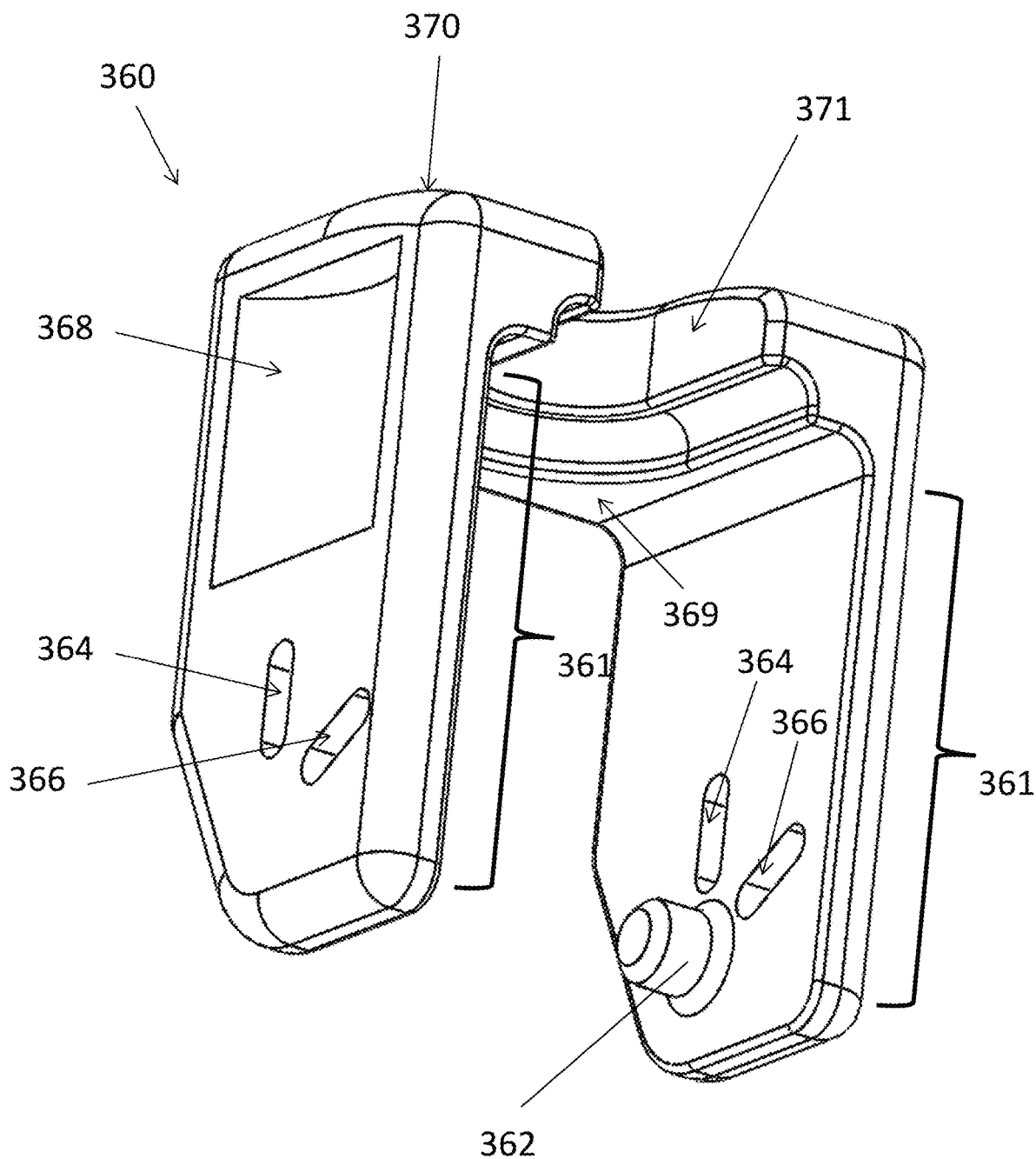
FIG. 9 is a perspective view of a swing spacer for use with microdose injection systems according to some embodiments.

As shown in FIG. 9, the swing spacer 360 includes a pair of arms 361. The swing spacer 360 also includes a pair of pivot pins 362 configured to be rotatably disposed in respective ones of the pair of side openings 342 in the finger flange such that the pair of pivot pins 362 and the corresponding pair of side openings 342 define a hinge about which the swing spacer 360 rotates relative to the finger flange 340. The diameter of the pivot pin 362 is sized to be smaller than the diameter of the side openings 342 to allow for axial movement of the swing spacer 360 such that during priming of the system 300, the plunger member 350 contacts the proximal surface 370 of the swing spacer 360, forcing the swing spacer 360 distally until the distally facing surface 369 of the swing spacer 360 contacts the proximal surface 346 of the finger flange 340. The distance between the proximal 370 and distal 369 surfaces of the swing spacer define distance 356 (see FIG. 9), which is the size of the dose of injectable fluid to be delivered. Distance 356 is also the distance between the proximal surface 370 of the swing spacer 360 and the proximal surface 346 of the finger flange 340 (see FIG. 12). The swing spacer 360 also includes respective pairs of aligned slots 364 and askew slots 366 configured to interfere with the pair of bumps 344 on the finger flange 342 removably retain the swing spacer in respective aligned and askew configurations as described herein. The swing spacer 360 further includes a proximal surface 370 configured to limit distal movement of the plunger member 350 relative to the finger flange 340 and the syringe body 310 to which the finger flange 340 is coupled when the swing spacer 360 is in the aligned configuration as described herein. The swing spacer 360 further includes a lateral slot 371 which is sized to allow the plunger member 350 distal end 351 to be inserted freely and is smaller than the stop 352 to prevent further insertion of the plunger member 350. The lateral slot 371 is further sized to allow rotation of the swing spacer 360 into an askew configuration whereby the plunger member 350 is allowed to move distally until the stop 352 contacts the proximal surface 346 of the finger flange 340. The swing spacer 360 includes a pair of indentations/finger grip surfaces 368 disposed where it is accessible to the user's fingers for applying a force to rotate the swing spacer 360 from the aligned to the askew configuration.

Figure 10:
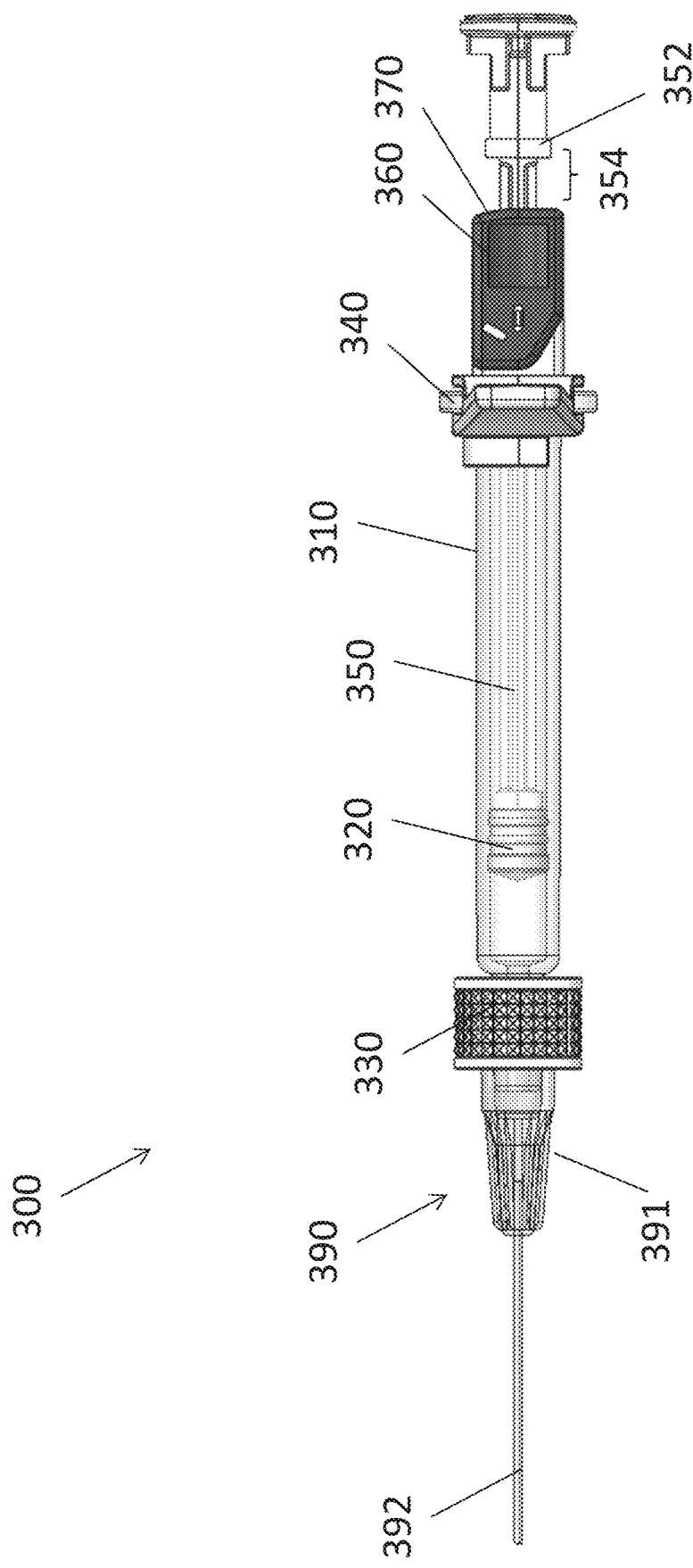
FIGS. 10 to 13 are side views of a microdose injection system in various configurations illustrating microdose injection methods according to some embodiments.

FIG. 10 depicts the microdose injection system 300 in a transport configuration in which the microdose injection system 300 is delivered to a user in a packaging. In some embodiments, the microdose injection system 300 in the transport configuration also includes a needle cover (not shown). FIG. 10 also shows the swing spacer 360 in the aligned configuration in which a longitudinal axis of the swing spacer 360 is aligned with a longitudinal axis of the syringe body 310. With the swing spacer 360 and the aligned configuration, the proximal surface 370 of the swing spacer 360 interferes with a stop 352 on the plunger member 350 to limit distal movement of the plunger member 350 relative to the syringe body 310. In the transport configuration, the plunger member 350 is positioned such that the stop 352 is disposed a distance 354 proximal of the proximal surface 370 of the swing spacer 360. This distance 354 is provided to allow the plunger member 350 to be advanced distally relative to the syringe body 310 to de-bubble/prime the microdose injection system 300 prior to injection. De-bubbling/priming the system 300 may include expelling air from the interior of the needle 392, and/or the needle hub 391, and/or the syringe body 310.

Figure 11:
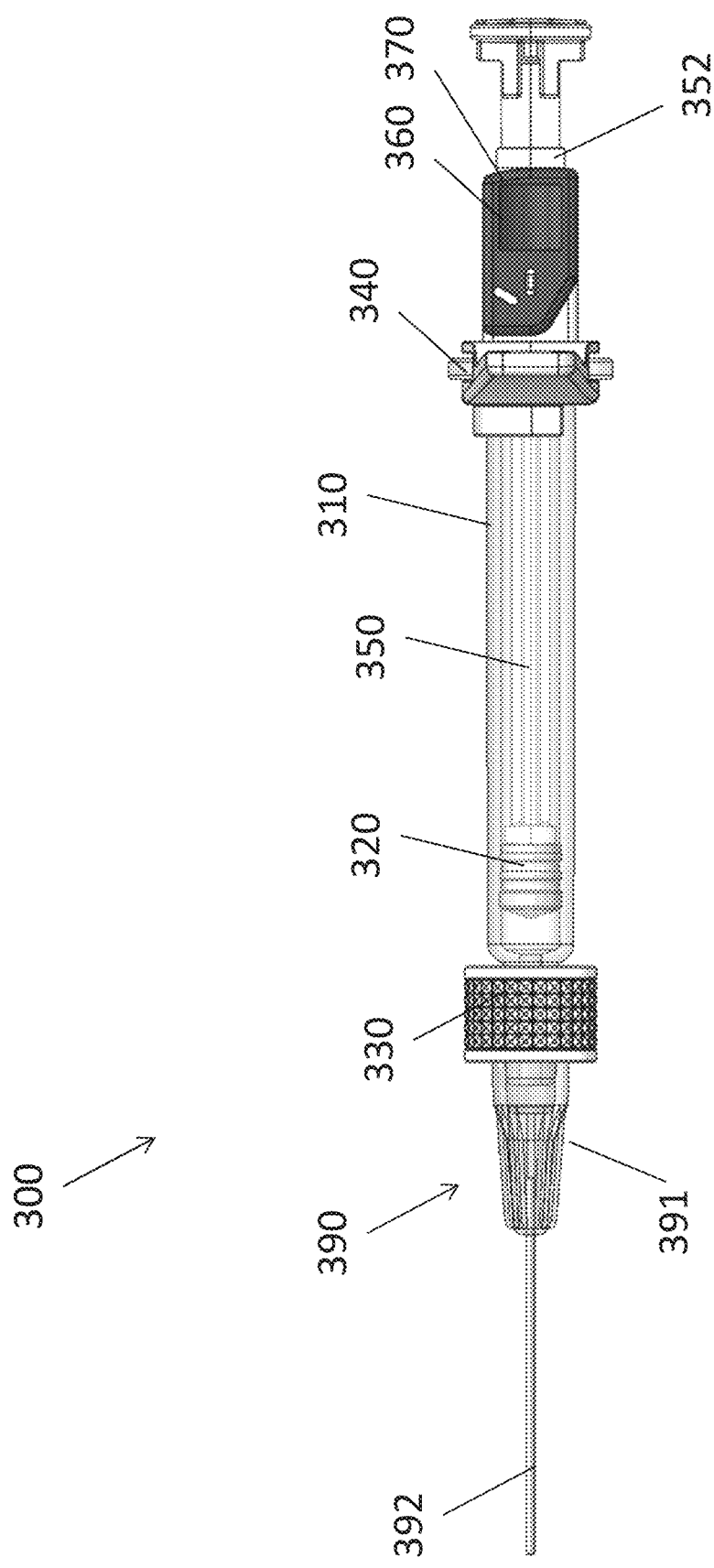

FIG. 11 depicts the microdose injection system 300 in a primed configuration. The microdose injection system 300 is transformed from the transport configuration shown in FIG. 10 to the primed configuration shown in FIG. 11 by first positioning the microdose injection system 380 upright/vertical orientation to move the gases/bubbles in the syringe body 310 distally near the distal needle interface 330, then applying a distally directed force to the plunger member 350 to move the plunger member 350 distally until the stop 352 on the plunger member 350 is in contact with the proximal surface 370 of the swing spacer 360. The stop 352 on the plunger member 350 is configured such that closing the distance 354 between the stop 352 and the proximal and 370 of the swing spacer 360 removes all of the gases/bubbles from the syringe body 310 and/or the needle assembly 390. The distance 354 can be tuned by modifying the positions of the plunger member at 350 and the stop 352 in the transport configuration to control the amount of gases/bubbles to be removed during de-bubbling.

Figure 12:
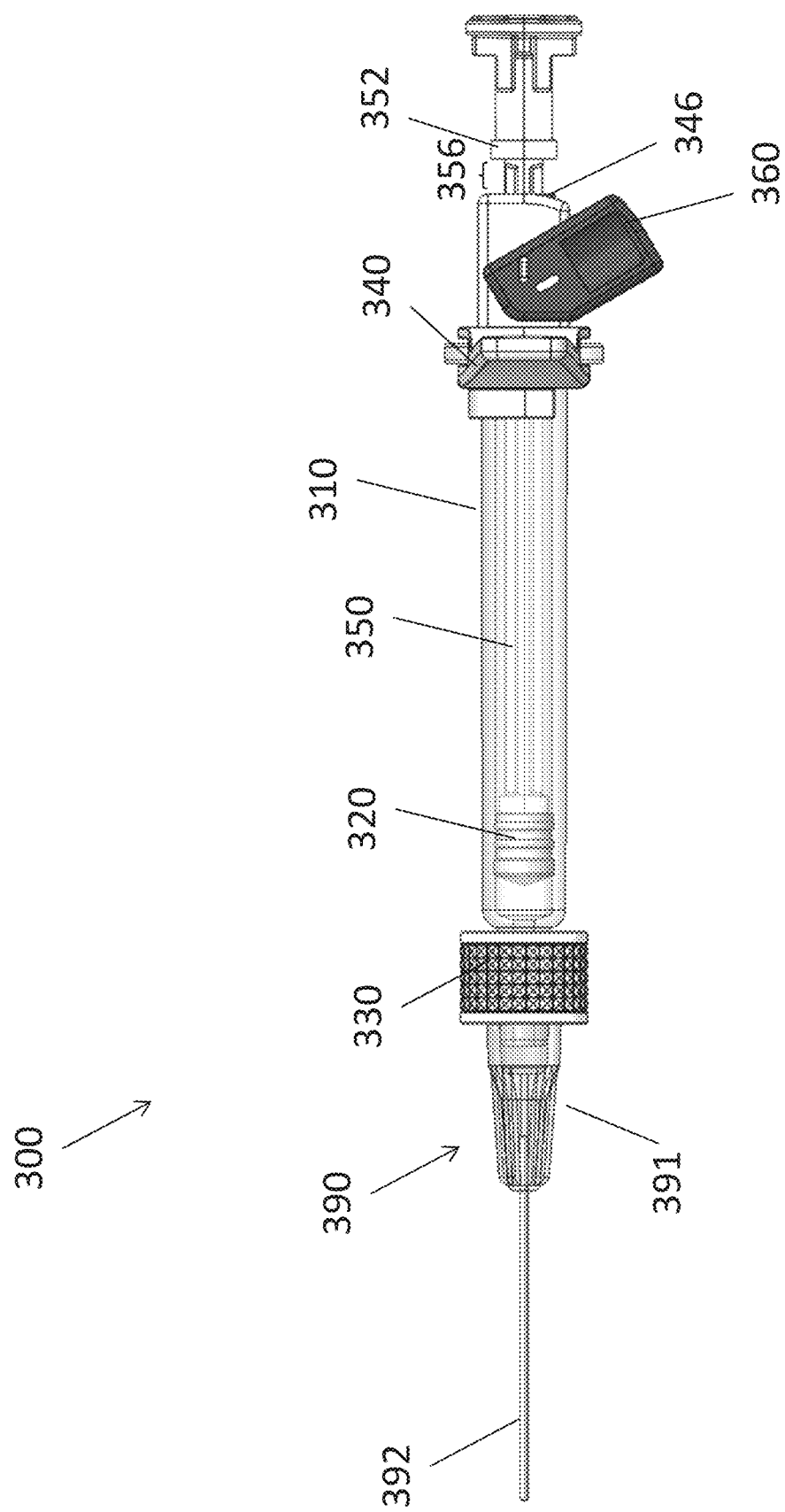

FIG. 12 depicts the microdose injection system 300 in an injection configuration. The microdose injection system 300 is transformed from the primed configuration shown in FIG. 11 to the injection configuration shown in FIG. 12 by moving the swing spacer 360 from the aligned configuration shown in FIG. 11 to the askew configuration shown in FIG. 12. In the askew configuration, the longitudinal axis of the swing spacer 360 is askew (e.g., about 60°) from the longitudinal axis of the syringe body 310. As shown in FIG. 12, the swing spacer 360 and the askew configuration does not interfere with distal movement of the plunger member 350 relative to the syringe body 310. Moving the swing spacer 360 from the aligned configuration to the askew configuration uncovers a distance 356 between the stop 352 on the plunger member 350 and the proximal surface 346 of the finger flange 340. The distance between the proximal 370 and distal 369 surfaces of the swing spacer define the plunger rod distance 356 (see FIGS. 9 and 12), which is the size of the dose of injectable fluid to be delivered by the microdose injection system 300. In the embodiment depicted in FIGS. 6 to 13, the dose of injectable fluid may be 50 µL. In other embodiments, the dose may be 20 to 500 µL.

Figure 13:
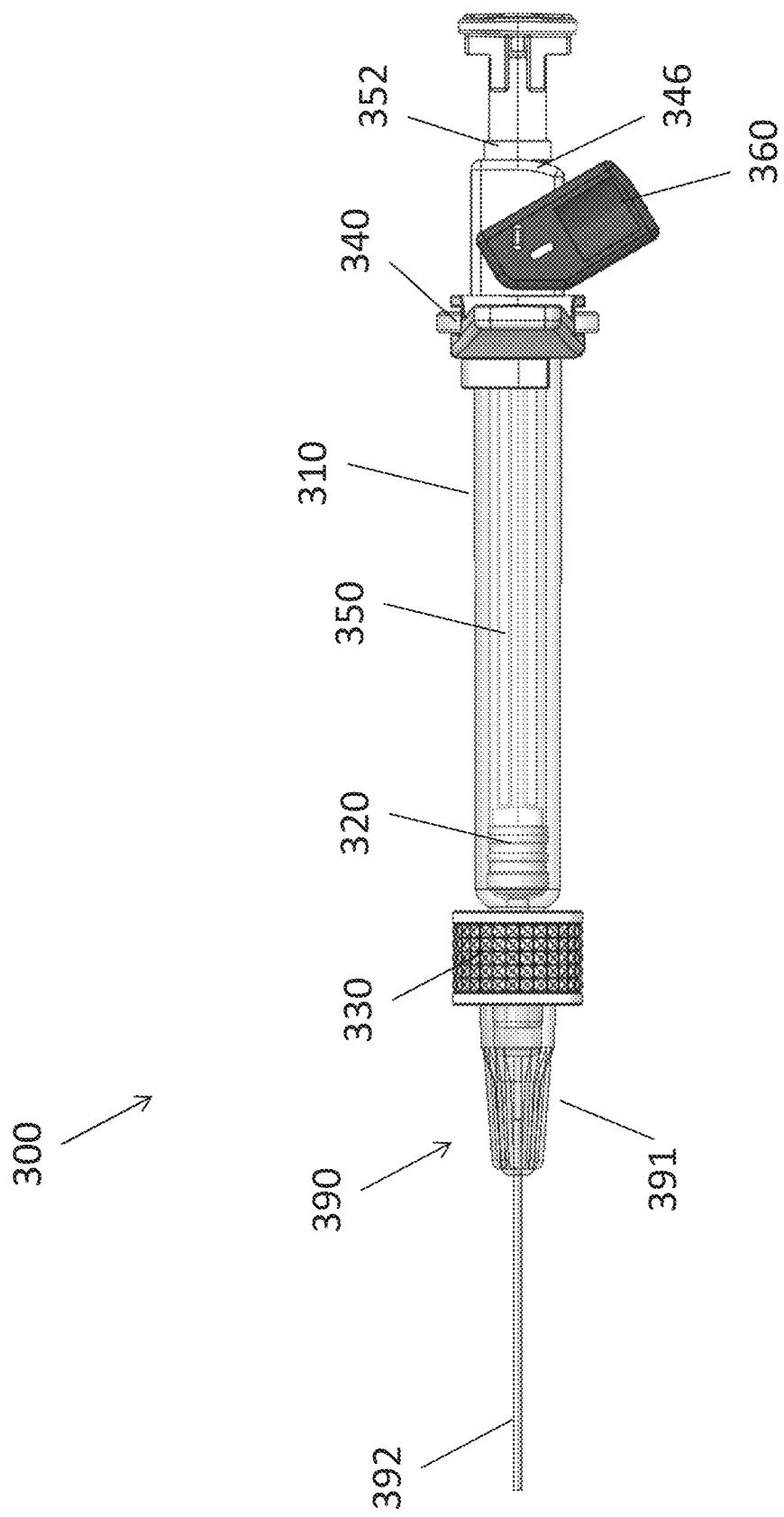

FIG. 13 depicts the microdose injection system 300 in a completed configuration. The microdose injection system 300 is transformed from the injection configuration shown in FIG. 12 to the completed configuration shown in FIG. 13 by first positioning a tip of the needle 392 coupled to the distal needle interface 330 in the injection targeted (e.g., patient), then applying a distally directed force to the plunger member 350 to move the plunger member 350 distally until the stop 352 on the plunger member 350 is in contact with the proximal surface 346 of the finger flange 340. The stop 352 on the plunger member 350 and the swing spacer 360 are configured such that closing the distance 356 between the stop 352 and the proximal surface 346 of the finger flange 340 delivers a predefined dose of injectable fluid from the syringe body 310. The distance 356 can be tuned by modifying the modifying the positions of the plunger member at 350 and the stop 352 and the size of the swing spacer 360 to control the size of the dose of injectable fluid.

After injection, a needle 392 attached to the distal needle interface 330 may be retracted such that the sharp tip thereof is contained within the needle assembly 390 to provide a safe microdose injection system. Examples of such safe injection systems are described in U.S. patent application Ser. No. 14/696,342, the contents of which have been previously Incorporated by reference herein.

Figure 14:
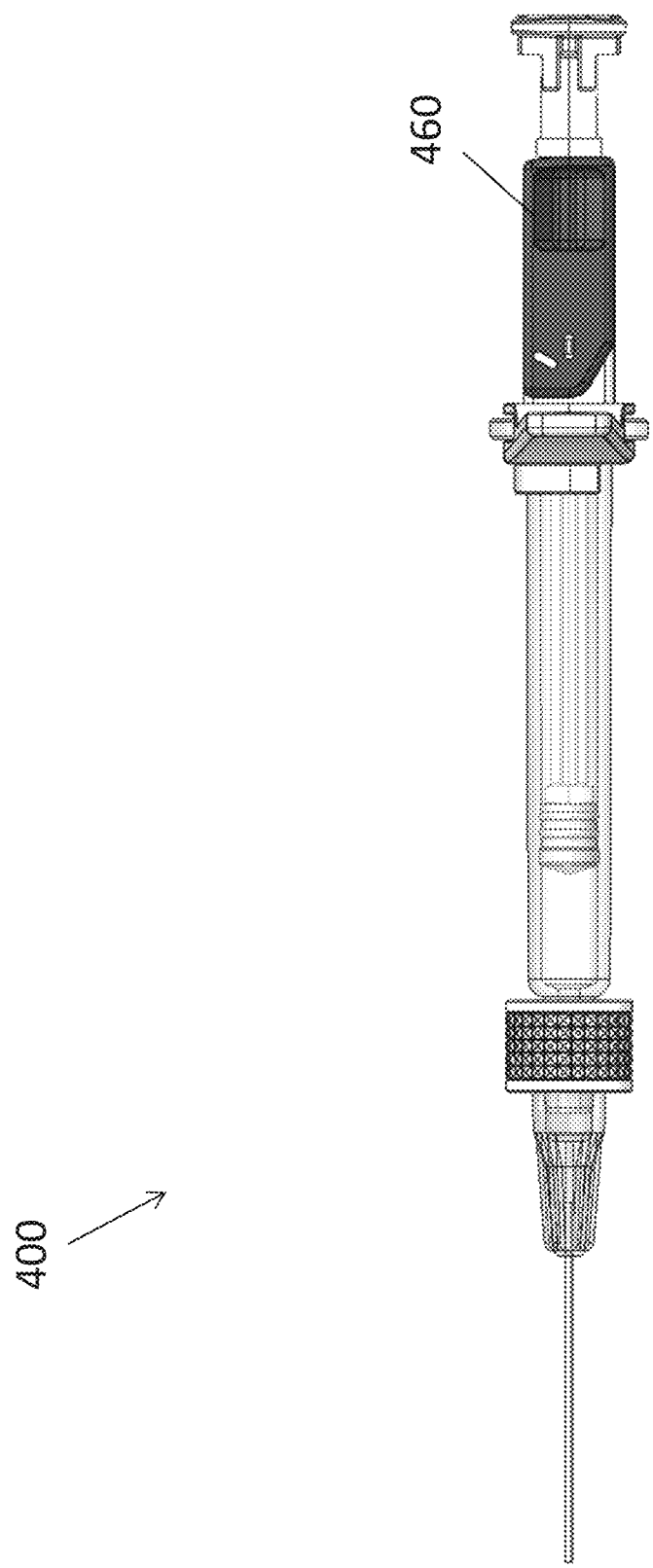
FIGS. 14 and 15 are side views of a microdose injection system and various configurations microdose injection methods according to some embodiments.
Figure 15:
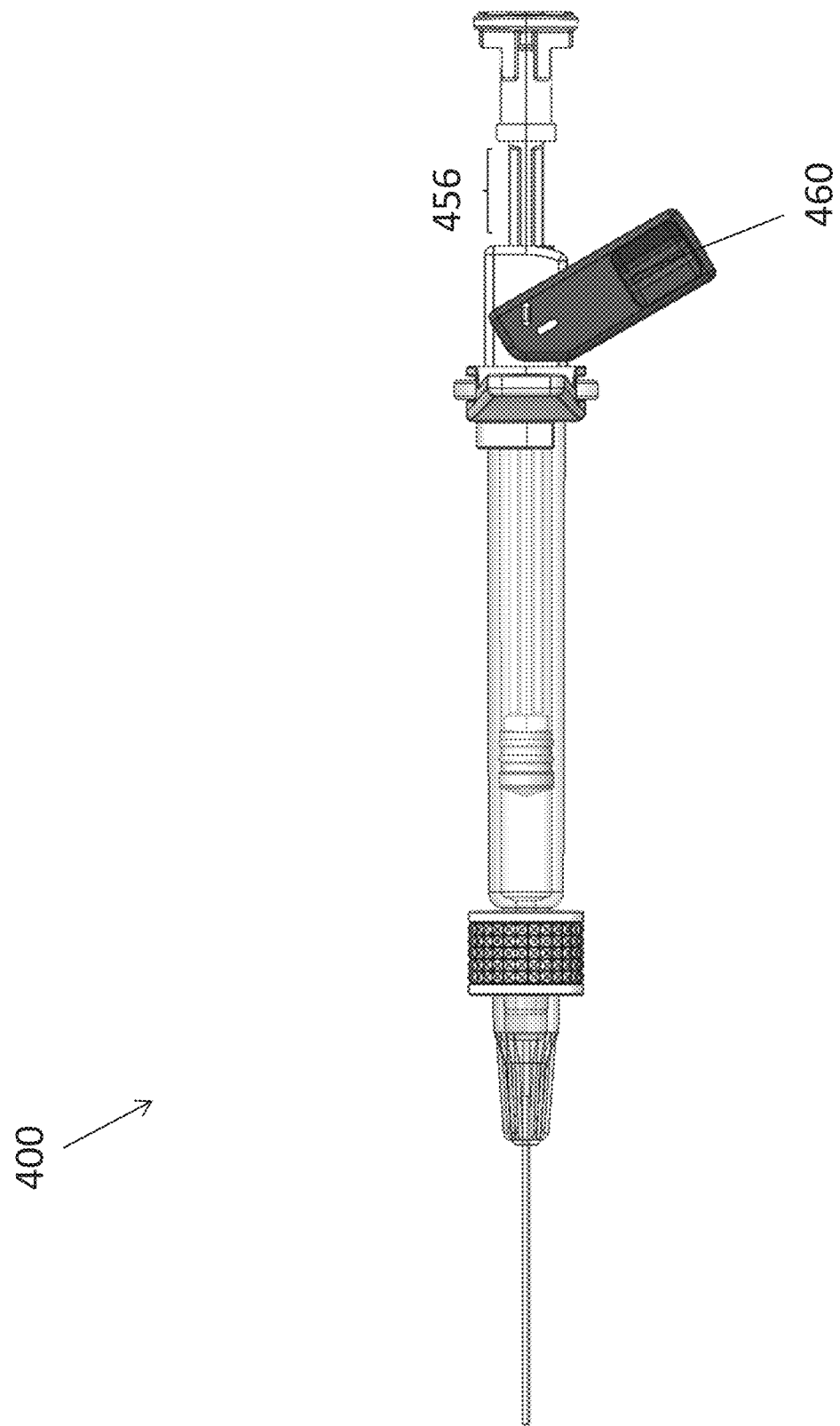

FIGS. 14 and 15 depict a microdose injection system 400 in the primed and injection configurations according to some other embodiments. The swing spacer 460 in the microdose injection system 400 is longer than the swing spacer 360 and the microdose injection system 300 depicted in FIGS. 6 to 13. The distance 456 between the proximal and distal surfaces of the swing spacer 460 is greater than the distance 356 depicted in FIGS. 9 and 12. Accordingly, the microdose injection system 400 is configured to deliver a larger (e.g., 165 µL) dose of an injectable fluid.

While various embodiments have been described with specific connectors (e.g., slip and Luer), these embodiments can be used with any known injection system connectors. While various embodiments have been described with staked needles and needle connectors, these embodiments can be used with any known permanently coupled needle or needle connector system.

Various exemplary embodiments of the invention are described herein. Reference is made to these examples in a non-limiting sense. They are provided to illustrate more broadly applicable aspects of the invention. Various changes may be made to the invention described and equivalents may be substituted without departing from the true spirit and scope of the invention. In addition, many modifications may be made to adapt a particular situation, material, composition of matter, process, process act(s) or step(s) to the objective(s), spirit or scope of the present invention. Further, as will be appreciated by those with skill in the art that each of the individual variations described and illustrated herein has discrete components and features which may be readily separated from or combined with the features of any of the other several embodiments without departing from the scope or spirit of the present inventions. All such modifications are intended to be within the scope of claims associated with this disclosure.

Any of the devices described for carrying out the subject diagnostic or interventional procedures may be provided in packaged combination for use in executing such interventions. These supply "kits" may further include instructions for use and be packaged in sterile trays or containers as commonly employed for such purposes.

The invention includes methods that may be performed using the subject devices. The methods may comprise the act of providing such a suitable device. Such provision may be performed by the end user. In other words, the "providing" act merely requires the end user obtain, access, approach, position, set-up, activate, power-up or otherwise act to provide the requisite device in the subject method. Methods recited herein may be carried out in any order of the recited events which is logically possible, as well as in the recited order of events.

Exemplary aspects of the invention, together with details regarding material selection and manufacture have been set forth above. As for other details of the present invention, these may be appreciated in connection with the above-referenced patents and publications as well as generally known or appreciated by those with skill in the art. For example, one with skill in the art will appreciate that one or more lubricious coatings (e.g., hydrophilic polymers such as polyvinylpyrrolidone-based compositions, fluoropolymers such as tetrafluoroethylene, PTFE, hydrophilic gel or silicones) may be used in connection with various portions of the devices, such as relatively large interfacial surfaces of movably coupled parts, if desired, for example, to facilitate low friction manipulation or advancement of such objects relative to other portions of the instrumentation or nearby tissue structures. The same may hold true with respect to method-based aspects of the invention in terms of additional acts as commonly or logically employed.

In addition, though the invention has been described in reference to several examples optionally incorporating various features, the invention is not to be limited to that which is described or indicated as contemplated with respect to each variation of the invention. Various changes may be made to the invention described and equivalents (whether recited herein or not included for the sake of some brevity) may be substituted without departing from the true spirit and scope of the invention. In addition, where a range of values is provided, it is understood that every intervening value, between the upper and lower limit of that range and any other stated or intervening value in that stated range, is encompassed within the invention.

Also, it is contemplated that any optional feature of the inventive variations described may be set forth and claimed independently, or in combination with any one or more of the features described herein. Reference to a singular item, includes the possibility that there are plural of the same items present. More specifically, as used herein and in claims associated hereto, the singular forms "a," "an," "said," and "the" include plural referents unless the specifically stated otherwise. In other words, use of the articles allow for "at least one" of the subject item in the description above as well as claims associated with this disclosure. It is further noted that such claims may be drafted to exclude any optional element. As such, this statement is intended to serve as antecedent basis for use of such exclusive terminology as "solely," "only" and the like in connection with the recitation of claim elements, or use of a "negative" limitation.

Without the use of such exclusive terminology, the term "comprising" in claims associated with this disclosure shall allow for the inclusion of any additional element—irrespective of whether a given number of elements are enumerated in such claims, or the addition of a feature could be regarded as transforming the nature of an element set forth in such claims. Except as specifically defined herein, all technical and scientific terms used herein are to be given as broad a commonly understood meaning as possible while maintaining claim validity.

The breadth of the present invention is not to be limited to the examples provided and/or the subject specification, but rather only by the scope of claim language associated with this disclosure.

What is claimed is:

1. A system for injecting, comprising:
   a syringe body having proximal and distal ends, a syringe interior, and a syringe flange at the proximal end thereof;
   an injectable fluid disposed in the syringe interior;
   a stopper member disposed in the syringe interior;
   a plunger member coupled to the stopper member;
   a finger flange removably coupled to the syringe flange, the finger flange defining a pair of side openings and a pair of bumps adjacent respective side openings; and
   a swing spacer rotatably coupled to the finger flange, the swing spacer defining a pair of arms, a pair of pivot pins, two pairs of slots, and a pair of indentations,
   wherein the swing spacer is configured to define a distance of movement of the plunger member relative to the syringe body along a longitudinal axis of the syringe body, thereby defining a dose of the injectable fluid.

2. The system of claim 1, wherein the pair of pivot pins on the swing spacer are disposed in the pair of side openings on the finger flange, such that the pair of side openings and the pair of pivot pins define a hinge about which the swing spacer rotates relative to the finger flange.

3. The system of claim 1, wherein the swing spacer has an aligned configuration wherein a longitudinal axis of the swing spacer is aligned with the longitudinal axis of the syringe body, and an askew configuration the longitudinal axis of the swing spacer is askew from the longitudinal axis of the syringe body.

4. The system of claim 3, wherein the swing spacer in the aligned configuration limits distal movement of the plunger member relative to the syringe body, and
   wherein the swing spacer in the askew configuration does not limit distal movement of the plunger member relative to the syringe body, such that the swing spacer is configured to define the distance of movement of the plunger member relative to the syringe body along the longitudinal axis of the syringe body, thereby defining the dose of the injectable fluid.

5. The system of claim 3, wherein the two pairs of slots on the swing spacer comprises two aligned slots and two askew slots,
   wherein the aligned slots are configured to interfere with the pair of bumps on the finger flange to removably retain the swing spacer in the aligned configuration, and
   wherein the askew slots are configured to interfere with the pair of bumps on the finger flange to removably retain the swing spacer in the askew configuration.

6. The system of claim 3, wherein the swing spacer further comprises a proximal surface when the swing spacer is in the aligned configuration, and
   wherein the plunger member comprises a stop configured to interfere with the proximal surface on the swing spacer in the aligned configuration to limit distal movement of the plunger member relative to the syringe body.

7. The system of claim 6, wherein the system has:
   a transport configuration in which the swing spacer is in the aligned configuration and the stop on the plunger member is disposed a distance proximal of the proximal surface of the swing spacer;
   a primed configuration in which the swing spacer is in the aligned configuration and the stop on the plunger member is in contact with the proximal surface of the swing spacer;
   an injection configuration in which the swing spacer is in the askew configuration and the stop on the plunger member is disposed a distance proximal of with a proximal surface of the finger flange; and
   a completed configuration in which the swing spacer is in the askew configuration and the stop on the plunger member is in contact with the proximal surface of the finger flange.

8. The system of claim 3, wherein the pair of indentations on the swing spacer are configured to facilitate user manipulation of the swing spacer to move the swing spacer between the aligned and askew configurations.

9. The system of claim 1, wherein the syringe body further comprises a distal needle interface configured to be coupled to a needle assembly having a needle.

10. A method for injecting a fluid, comprising:
    providing a syringe assembly, the syringe assembly comprising
    a syringe body having proximal and distal ends, a syringe interior, a distal needle interface at the distal end thereof, and a syringe flange at the proximal end thereof,
    an injectable fluid disposed in the syringe interior,
    a stopper member disposed in the syringe interior,
    a plunger member coupled to the stopper member,
    a finger flange removably coupled to the syringe flange, the finger flange defining a pair of side openings and a pair of bumps adjacent respective side openings, and a swing spacer rotatably coupled to the finger flange, the swing spacer defining a pair of arms, a pair of pivot pins, two pairs of slots, and a pair of indentations, the swing spacer being in an aligned configuration wherein a longitudinal axis of the swing spacer is aligned with a longitudinal axis of the syringe body;

moving the swing spacer from the aligned configuration to an askew configuration wherein the longitudinal axis of the swing spacer is askew from the longitudinal axis of the syringe body;

applying a distally directed force to a proximal end of the plunger member to expel a portion of the injectable fluid from the syringe interior through the distal needle interface.

11. The method of claim 10, wherein the syringe assembly has:
- a transport configuration in which the swing spacer is in the aligned configuration and a stop on the plunger member is disposed a distance proximal of a proximal surface of the swing spacer;
- a primed configuration in which the swing spacer is in the aligned configuration and the stop on the plunger member is in contact with the proximal surface of the swing spacer;
- an injection configuration in which the swing spacer is in the askew configuration and the stop on the plunger member is disposed a distance proximal of with a proximal surface of the finger flange; and
- a completed configuration in which the swing spacer is in the askew configuration and the stop on the plunger member is in contact with the proximal surface of the finger flange.

12. The method of claim 11, wherein the syringe assembly is provided in the transport configuration, the method further comprising:
- positioning the syringe assembly in the transport configuration in an upright orientation before moving the swing spacer from the aligned configuration to the askew configuration; and
- applying a distally directed force to the proximal end of the plunger member to expel a gas from the syringe interior through the distal needle interface to transform the syringe assembly from the transport configuration to the primed configuration before moving the swing spacer from the aligned configuration to the askew configuration, wherein moving the swing spacer from the aligned configuration to the askew configuration transforms the syringe assembly from the primed configuration to the injection configuration, and wherein applying the distally directed force to the proximal end of the plunger member to expel the portion of the injectable fluid from the syringe interior through the distal needle interface transforms the syringe assembly from the injection configuration to the completed configuration.

13. The method of claim 10, wherein the swing spacer in the aligned configuration limits distal movement of the plunger member relative to the syringe body, and
- wherein the swing spacer in the askew configuration does not limit distal movement of the plunger member relative to the syringe body, such that the swing spacer is configured to define a distance of movement of the plunger member relative to the syringe body along the longitudinal axis of the syringe body, thereby defining a dose of the injectable fluid.

14. The method of claim 10, wherein the two pairs of slots on the swing spacer comprises two aligned slots and two askew slots,
- wherein the aligned slots are configured to interfere with the pair of bumps on the finger flange to removably retain the swing spacer in the aligned configuration, and
- wherein the askew slots are configured to interfere with the pair of bumps on the finger flange to removably retain the swing spacer in the askew configuration.

15. The method of claim 10, moving the swing spacer from the aligned configuration to the askew configuration comprises grasping the pair of indentations on the swing spacer.

* * * * *